(12) United States Patent
Fukuchi (10) Patent No.: US 8,318,449 B2
(45) Date of Patent: Nov. 27, 2012

(54) METHOD OF MEASURING THE ACTIVITY OF LIPID-MODIFIED ENZYME

(75) Inventor: Naoyuki Fukuchi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 260 days.

(21) Appl. No.: 12/619,457

(22) Filed: Nov. 16, 2009

(65) Prior Publication Data

US 2010/0136578 A1 Jun. 3, 2010

Related U.S. Application Data

(63) Continuation of application No. PCT/JP2008/058930, filed on May 15, 2008.

(30) Foreign Application Priority Data

May 17, 2007 (JP) .................................. 2007-132169

(51) Int. Cl.
*C12Q 1/60* (2006.01)
(52) U.S. Cl. .................. 435/11; 435/19; 435/4; 435/21; 435/17; 435/15
(58) Field of Classification Search .................... 435/11, 435/4, 19, 21
See application file for complete search history.

(56) References Cited

U.S. PATENT DOCUMENTS

| | | | |
|---|---|---|---|
| 5,972,595 A * | 10/1999 | Kasila et al. ...................... 435/4 |
| 6,066,446 A | 5/2000 | Mullinax et al. | |
| 6,221,841 B1 | 4/2001 | Czech et al. | |
| 7,067,269 B2 | 6/2006 | Drees et al. | |
| 2005/0009124 A1 | 1/2005 | Drees et al. | |

FOREIGN PATENT DOCUMENTS

| JO | 2004-525964 | 8/2004 |
|---|---|---|
| WO | 02/083658 A1 | 10/2002 |
| WO | WO 03/047575 A1 | 6/2003 |
| WO | 2006/012093 A1 | 2/2006 |

OTHER PUBLICATIONS

Iiri et al. "Potentiation of Gi-mediated phospholipase C activation by retinoic acid in HL-60 cells", JBC, 1995, 270(11):5901-5908.*
Colin G. Ferguson, et al., "Phosphoinositide-Containing Polymerized Liposomes: Stable Membrane-Mimetic Vesicles for Protein-Lipid Binding Analysis", Bioconjugate Chemistry, vol. 16, No. 6, XP002576679, Nov. 2005, pp. 1475-1483.
"Phospholipase $A_2$ [$^3$H] SPA enzyme assay", Amersham Biosciences UK Limited 2003. Retrived from the Internet: http://www5.gelifesciences.com/aptrix/upp00919.nsf/Content/3424E007F6B590E7C1256EB40044AC15/$file/TRKQ7040PL.pdf.
Rueckle et al., P13Kγ inhibition: towards an 'aspirin of the $21^{st}$ century'?, Nat.Rev.Drug Discovery, vol. 5, Nov. 2006, pp. 903-918.
Maier et al.,"Roles of non-catalytic subunits in Gβγ-induced activation of class I phosphoinositide 3-kinase isoforms β and γ" The Journal of Biological Chemistry, vol. 274, No. 41, Issue of Oct. 8, 1999, pp. 29311-29317.
Buck et al.,"Modular design of Gβ as the basis for reversible specificity in effector stimulation", The Journal of Biological Chemistry, vol. 276, No. 38, Issue of Sep. 21, 2001, pp. 36014-36019.
Wettschureck et al., "Mammalian G proteins and their cell type specific functions", Physiolo. Rev. 85, (2005), pp. 1159-1204.
Bonacci et al., "Differential targeting of Gβ γ- subunit signaling with small molecules", Science, vol. 312, Apr. 21, 2006, pp. 443-446.
Parish et al., "Functional significance of βγ-subunit carboxymethylation for the activation of phospholipase C and phosphoinositide 3-kinase", Biochemestry 34, (1995), pp. 7722-7727.
Gray et al., "Nonradioactive methods for the assay of phosphoinositide 3-kinases and phosphoinositide phosphatases and selective detection of signaling lipids in cell and tissue extracts", Analytical Biochemisry 313, (2003), pp. 234-245.
Yoe-Sik et al., "Identification of a compound that directly stimulates phospholipase C activity", Molecular Pharmacology, vol. 63, No. 5, pp. 1043-1050, 2003.
J. Musti et al., "Specific surface association of avidin with N-biotinylphosphatidylethanolamine membrane assemblies: effect on lipid phase behavior and acyl-chain dynamics", Biochemistry 2001, 40, pp. 14869-14877.
Perker et al., "Affinity purification of lipid vesicles", Biotechnol. Prog., 2004, 20, pp. 262-268.
Davidson et al., "The biotin-capture lipid affinity assay: a rapid method for determining lipid binding parameters for apolipoproteins", Journal of Lipid Research, vol. 47, 2006, pp. 440-449.

* cited by examiner

*Primary Examiner* — Susan Hanley
*Assistant Examiner* — Bin Shen
(74) *Attorney, Agent, or Firm* — Oblon, Spivak, McClelland, Maier & Neustadt, L.L.P.

(57) ABSTRACT

It is intended to provide an assay method whereby the activity of a lipid-modifying enzyme can be conveniently measured over a wide range and a drug capable of controlling a lipid-modifying enzyme with the use of this assay method. The above problem can be solved by, for example, a method of measuring the activity of a lipid-modifying enzyme which comprises the steps of (I) preparing a lipid micelle containing a biotinylated lipid and a substrate for the lipid-modifying enzyme; (II) bringing the lipid micelle prepared in the above step (I) into contact with the lipid-modifying enzyme; and (III) evaluating the activity of the lipid-modifying enzyme by applying an evaluation method using the proximity effect to the product obtained in the above step (II).

15 Claims, 4 Drawing Sheets

(a) Reaction by PI3-kinase β using PIP2 micelle (b) Reaction by PI3-kinase β using PIP2/Biotin-PE micelle

SEQUENCE LISTING

```
<160> NUMBER OF SEQ ID NOS: 11

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggggatccg ccaccatgag tgagcttgac cagttac                                   37

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggctcgagg gcgttagttc cagatctt                                             28

<210> SEQ ID NO 3
<211> LENGTH: 1051
```

```
<212> TYPE: DNA
<213> ORGANISM: Homo sapiens

<400> SEQUENCE: 3
gggggatccg ccaccatgag tgagcttgac cagttacggc aggaggccga gcaacttaag      60
aaccagattc gagacgccag gaaagcatgt gcagatgcaa ctctctctca gatcacaaac     120
aacatcgacc cagtgggaag aatccaaatg cgcacgagga ggacactgcg ggggcacctg     180
gccaagatct acgccatgca ctggggcaca gactccaggc ttctcgtcag tgcctcgcag     240
gatggtaaac ttatcatctg ggacagctac accaccaaca aggtccacgc catccctctg     300
cgctcctcct gggtcatgac ctgtgcatat gccccttctg gaactatgt ggcctgcggt      360 ggcctggata cattttgctc catttacaat ctgaaaactc gtgaggggaa cgtgcgcgtg     420
agtcgtgagc tggcaggaca cacaggttac ctgtcctgct gccgattcct ggatgacaat     480
cagatcgtca ccagctctgg agacaccacg tgtgccctgt gggacatcga gaccggccag     540
cagacgacca cgtttaccgg acacactgga gatgtcatga gcctttctct tgctcctgac     600
accagactgt tcgtctctgg tgcttgtgat gcttcagcca aactctggga tgtgcgagaa     660
ggcatgtgcc ggcagacctt cactggccac gagtctgaca tcaatgccat ttgcttcttt     720
ccaaatggca atgcatttgc cactggctca gacgacgcca cctgcaggct gtttgacctt     780
cgtgctgacc aggagctcat gacttactcc atgacaacaa tcatctgcgg gatcacctct     840
gtctccttct ccaagagcgg gcgcctcctc cttgctgggt acgacgactt caactgcaac     900
gtctgggatg cactcaaagc cgaccgggca ggtgtcttgg ctgggcatga caaccgcgtc     960
agctgcctgg gcgtgactga cgatggcatg gctgtggcga cagggtcctg ggatagcttc    1020
ctcaagatct ggaactaacg ccctcgagcc c                                    1051

<210> SEQ ID NO 4
<211> LENGTH: 340
<212> TYPE: PRT
<213> ORGANISM: Homo sapiens

<400> SEQUENCE: 4

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
```

```
              165                 170                 175
Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 5
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggggatccg ccaccatggc ccatcaccat caccatcacg ccgccagcaa caacaccgcc    60
ag                                                                  62

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttctcgagtt aaaggatggc acagaaaaac ttc                                 33

<210> SEQ ID NO 7
<211> LENGTH: 263
<212> TYPE: DNA
<213> ORGANISM: Homo sapiens

<400> SEQUENCE: 7
gggggatccg ccaccatggc ccatcaccat caccatcacg ccgccagcaa caacaccgcc    60
agcatagcac aagccaggaa gctggtagag cagcttaaga tggaagccaa tatcgacagg   120
ataaaggtgt ccaaggcagc tgcagatttg atggcctact gtgaagcaca tgccaaggaa   180
gacccccctc ctgaccctgt tccggcttca gaaaaccgt ttagggagaa gaagtttttc    240
tgtgccatcc tttaactcga gaa                                           263
```

<210> SEQ ID NO 8
<211> LENGTH: 79
<212> TYPE: PRT
<213> ORGANISM: Homo sapiens

<400> SEQUENCE: 8

```
Met Ala His His His His His His Ala Ala Ser Asn Asn Thr Ala Ser
1               5                   10                  15

Ile Ala Gln Ala Arg Lys Leu Val Glu Gln Leu Lys Met Glu Ala Asn
            20                  25                  30

Ile Asp Arg Ile Lys Val Ser Lys Ala Ala Asp Leu Met Ala Tyr
        35                  40                  45

Cys Glu Ala His Ala Lys Glu Asp Pro Leu Leu Thr Pro Val Pro Ala
    50                  55                  60

Ser Glu Asn Pro Phe Arg Glu Lys Lys Phe Phe Cys Ala Ile Leu
65                  70                  75
```

<210> SEQ ID NO 9
<211> LENGTH: 21
<212> TYPE: PRT
<213> ORGANISM: Homo sapiens

<400> SEQUENCE: 9

```
Cys Gly Gly Tyr Met Asp Met Ser Lys Asp Glu Ser Val Asp Tyr Val
1               5                   10                  15

Pro Met Leu Asp Met
            20
```

<210> SEQ ID NO 10
<211> LENGTH: 11
<212> TYPE: PRT
<213> ORGANISM: Rattus norvegicus

<400> SEQUENCE: 10

```
Asn Gly Asp Tyr Met Pro Met Ser Pro Lys Ser
1               5                   10
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

```
His His His His His His
1               5
```

METHOD OF MEASURING THE ACTIVITY OF LIPID-MODIFIED ENZYME

CROSS-REFERENCE TO RELATED APPLICATIONS

The present application is a continuation of International patent application PCT/JP2008/058930, filed on May 15, 2008, which claims priority to Japanese patent application JP 2007-132169, filed on May 17, 2007, which are incorporated herein by reference in their entireties.

TECHNICAL FIELD

The present invention relates to a method of assaying the activity of a lipid-modifying enzyme, a method of screening an inhibitor or activator of the lipid-modifying enzyme using this assay method, a lipid micelle containing a biotinylated lipid and a substrate for the lipid-modifying enzyme which can be used in these methods, and the like.

BACKGROUND ART

Lipid-modifying enzymes such as phosphoinositide kinases, phosphoinositide phosphatases, phospholipases, etc., which induce structural changes (modifications) of lipid molecules on cell membranes, are enzymes involved in cell signaling and evoke diverse cellular responses due to the changes in actions of these lipid-modifying enzymes accompanied by stimulation to the cells. These lipid-modifying enzymes are targeted by various therapeutic drugs, and screening studies have been widely conducted especially on inhibitors/activators. For example, phosphoinositide 3-kinase γ, which is one of phosphoinositide kinases, has been extensively studied as a target molecule for an anti-inflammatory drug (e.g., Non-Patent Literature 1: T. Rückle et al., Nat. Rev. Drug Discovery, 5, 903 (2006)).

In recent years, it has been discovered that the activities of these lipid-modifying enzymes in cell signaling are regulated through the interactions with proteins present on cell membranes.

Examples of the combination of lipid-modifying enzymes and cell membrane proteins controlling the activities are shown in TABLE 1 (Non-Patent Literature 2: U. Maier et al., JBC, 274, 29311 (1999), Non-Patent Literature 3: Ref: E. Buck and R. R. Iyengar, J. Biol. Chem., 276, 36014 (2001) and Non-Patent Literature 4: N. Wittschureck and S. Offermanns, Physiol. Rev., 85, 1159 (2005)).

TABLE 1

Examples of lipid-modifying enzymes and controlling cell membrane proteins

| Lipid-Modifying Enzyme | Controlling Cell Membrane Protein |
| --- | --- |
| Phosphoinositide-3-kinase α | Tyr-phosphorylated receptor |
| Phosphoinositide-3-kinase β | Tyr-phosphorylated proteins, G-protein βγ subunits |
| Phosphoinositide-3-kinase γ | G-protein βγ subunits |
| Phosphoinositide-3-kinase δ | Tyr-phosphorylated proteins |
| Phospholipase C β | G-protein αq subunits, G-protein βγ subunits |
| Phospholipase C γ | Tyr-phosphorylated proteins |

Accordingly, drugs to treat diseases by controlling the activities of these lipid-modifying enzymes can directly target their modifying reactions (namely, target the interactions between lipid substrates, ATP, etc. and enzymes) and additionally can target the interactions between these enzymes and cell membrane proteins which control the enzymes. However, such drugs have little been developed so far. Extensive development of drugs is ongoing in, for example, phosphoinositide 3-kinase γ described above, which act on the enzyme to exhibit an anti-inflammatory action, but these drugs basically bind to the ATP-binding site and directly inhibit the modifying reactions (cf., Non-Patent Literature 1).

One of the reasons is that methods for assaying the interactions between a lipid-modifying enzyme and a cell membrane protein regulating the enzyme are not simple. In other words, to assay for such interactions, a lipid served as substrate should be present in the form of a lipid micelle so that studies to investigate such interactions have all been carried out using lipid micelles. However, in most studies using lipid micelles as substrate, methods to extract lipids resulting from the reaction with a solvent are employed. These methods are unsuitable for screening to find a controlling drug.

For example, the following methods are known for assaying the activities of lipid-modifying enzymes.

To assay the activity of phosphoinositide 3-kinase, conventional methods are used which involve preparing lipid micelles containing molecules served as substrate, such as phosphatidylinositol (PI), phosphatidylinositol [4,5]-diphosphate (PIP2), etc., reacting the lipid micelles using $^{32}$P and $^{33}$P-ATP, extracting the lipids with an organic solvent and finally separating and quantifying the produced phosphatidylinositol monophosphate (PIP) or phosphatidylinositol [3,4,5]-triphosphate (PIP3) by thin layer chromatography, etc. (e.g., Non-Patent Literature 5: T. M. Bonacci et al., Science, 312, 443 (2006), Non-Patent Literature 6: U. Maier et al., J. Biol. Chem., 274, 29311 (1999) and Non-Patent Literature 7: C. A. Parish et al., Biochemistry, 34, 7722 (1995)).

Alternatively, a simple assay method using the proximity effect is also used, which involves "indirect" detection and quantization of PIP3 produced through the reaction of soluble PIP2 as substrate with non-radioisotope ATP by using as an indicator the ability to compete for binding biotinylated soluble PIP3 to PIP3-binding proteins (e.g., Non-Patent Literature 8: A. Gray et al., Anal. Biochem., 313, 234 (2003), Patent Literature 1: B. E. Drees et al., U.S. Pat. No. 7,067,269 and Patent Literature 2: B. E. Drees et al., US Patent 2005/0009124). However, the substrate is soluble PIP2. Application of this method using a lipid-micellized substrate is not reported and it is considered difficult to apply said method to an assay using lipid micelles as a substrate.

In addition, a method which involves immobilizing PIP2 as substrate on FlashPlate where phospholipids have been immobilized and measuring the uptake of $^{33}$P from $^{33}$P-ATP (e.g., Non-Patent Literature 9: PerkinElmer Inc., Scientific Poster #H78394), a method which involves binding lipid micelles containing substrate to SPA (scintillation proximity assay) beads through an electrostatic or hydrophobic interaction and similarly measuring the $^{33}$P uptake, and the like are reported as simple assay methods using the proximity effect (e.g., Non-Patent Literature 10: GE Healthcare Life Sciences, Inc., Scientific Poster #132). However, since immobilization of PIP2 onto FlashPlate or binding of lipid micelles to SPA beads is based on an electrostatic or hydrophobic interaction, it is easy to envisage the drawbacks that substrate molecules are poorly incorporated, the immobilization or binding is susceptible to surfactant effect, etc. These assay methods are scarcely used for practical applications, which is clear also from very few reports in literatures or the like.

Also, a method for assaying the activity of phospholipase which involves preparing lipid micelles containing $^3$H-labeled PIP2 and measuring the enzymatically hydrolyzed inositol triphosphate (IP3) left in an aqueous layer through organic solvent extraction is used in general (e.g., Non-Patent Literature 11: B. Yoe-Sik et al., Mol. Pharm., 63, 1043 (2003)).

Furthermore, an assay kit is put in practical use for a simple assay method, which involves preparing lipid micelles containing [$^3$H]-PIP2 having a biotinyl group in the molecule, carrying out the reaction with phospholipase, adding streptavidin-coated SPA beads and determining the level of $^3$H remained on the lipid micelles without solvent extraction (e.g., Non-Patent Literature 12: GE Healthcare Inc., Product No. TRKQ7040, protocol attached). This method using the compound containing in its molecule the biotin residue and the substrate residue susceptible to the actions of lipid-modifying enzyme might be used for measurement of the activities of other lipid-modifying enzymes than phospholipase, if the substrate residue part is changed. For this purpose, however, it is necessary to synthesize, for each enzyme, a compound with a biotin residue introduced in the molecule, not a readily available substrate for lipid-modifying enzyme, which makes any simple measurement difficult.

The foregoing problems involved in the prior art are summarized below.

(1) In the assay system for screening a controlling substance for lipid-modifying enzymes, evaluation including the interactions with controlling cell membrane proteins can be made only when lipid micelles containing lipids served as a substrate are prepared and used as the substrate. In general, a complicated (low-throughput) assay method for measuring the amount of a substrate changed through the reaction using a radioisotope followed by solvent extraction is used for the evaluation of lipid-modifying enzymes, especially "including interactions with cell membrane proteins to be controlled."

(2) The following methods are known as homogeneous assay methods using lipid micelles containing lipids which are served as a substrate:

a) for phosphoinositide kinases, a method which comprises immobilizing the micelles to beads or plates using an electrostatic or hydrophobic binding function; and, b) for phospholipases, a method using a compound containing both the biotin residue and a residue served as an enzyme substrate in the same molecule. However, it is readily expected for the method a) that the immobilizing efficiency is poor or the effects of a surfactant are significant. In the method b), it is necessary to design and synthesize a compound suitable for the enzyme in a creative way. Any of these methods is simply not applicable to a variety of "lipid-modifying enzymes."

Regarding lipid micelles containing biotinylated lipids such as biotinylated phosphatidylethanolamine, etc., it is known that biotin-binding proteins such as streptavidin, etc. bind onto the micelles (e.g., Non-Patent Literature 13: J. Musti et al., Biochemistry, 40, 14869 (2001)) and the micelles bind to a carrier, where biotin binding proteins such as streptavidin, etc. are immobilized (e.g., Non-Patent Literature 14: B. Peker et al., Biotechnol. Prog., 20, 262 (2004)). There is a report on, for example, the measurement of the binding function of proteins bound onto the micelles by applying this method (e.g., Non-Patent Literature 15: W. S. Davidson et al., J. Lipid Res., 47, 440 (2006)).

[Non-Patent Literature 1] T. Rückle et al., Nat. Rev. Drug Discovery, 5, 903 (2006)

[Non-Patent Literature 2] U. Maier et al., JBC, 274, 29311 (1999)

[Non-Patent Literature 3] Ref: E. Buck and R. R. Iyengar, J. Biol. Chem., 276, 36014 (2001)

[Non-Patent Literature 4] N. Wittschureck and S. Offermanns, Physiol. Rev., 85, 1159 (2005)

[Non-Patent Literature 5] T. M. Bonacci et al., Science, 312, 443 (2006)

[Non-Patent Literature 6] U. Maier et al., J. Biol. Chem., 274, 29311 (1999)

[Non-Patent Literature 7] C. A. Parish et al., Biochemistry, 34, 7722 (1995)

[Non-Patent Literature 8] A. Gray et al., Anal. Biochem., 313, 234 (2003)

[Patent Literature 1] B. E. Drees et al., U.S. Pat. No. 7,067, 269

[Patent Literature 2] B. E. Drees et al., US patent 2005/ 0009124

[Non-Patent Literature 9] PerkinElmer Inc., Scientific Poster #H78394

[Non-Patent Literature 10] GE Healthcare Life Sciences, Inc., Scientific Poster #132

[Non-Patent Literature 11] B. Yoe-Sik et al., Mol. Pharm., 63, 1043 (2003)

[Non-Patent Literature 12] GE Healthcare Life Sciences, Inc., Product No. TRKQ7040, Attached Protocol

[Non-Patent Literature 13] J. Musti et al., Biochemistry, 40, 14869 (2001)

[Non-Patent Literature 14] B. Peker et al., Biotechnol. Prog., 20, 262 (2004)

[Non-Patent Literature 15] W. S. Davidson et al., J. Lipid Res., 47, 440 (2006)

DISCLOSURE OF INVENTION

Under these circumstances, a simple method for assaying the activity of a lipid-modifying enzyme and a simple method for screening a substance (inhibitor or promotor) capable of controlling the activity of the lipid-modifying enzyme have been desired for a wide range of lipid-modifying enzymes. Furthermore, a simple screening method using a lipid micelle as a substrate has been desired in order to evaluate lipid-modifying enzymes including the interactions between cell membrane-associated proteins controlling activities of these lipid-modifying enzymes and the lipid-modifying enzymes.

In view of the foregoing circumstances, the present inventor has made extensive investigations in the model assay system using phosphoinositide 3-kinase as the lipid-modifying enzyme, biotinyl phosphatidylethanolamine as the biotinylated lipid and phosphatidylinositol [4,5]-diphosphate (PIP2) as the lipid-modifying enzyme substrate. As a result, the inventor has succeeded in developing the assay principle A) for a wide range of lipid-modifying enzymes B) that can simply measure the enzyme reactants produced by the reaction using lipid micelles C) by the assay method using the proximity effect. The present invention has thus been accomplished.

In other words, the present invention provides a method of assaying the activity of a lipid-modifying enzyme, a method of screening a substance which inhibits or promotes the activity of the lipid-modifying enzyme, and so on, which are described below.

(1) A method of assaying the activity of a lipid-modifying enzyme, which comprises the steps of:

(i) bringing a lipid micelle containing a biotinylated lipid and a substrate for the lipid-modifying enzyme into contact with the lipid-modifying enzyme; and, (ii) evaluating the activity of the lipid-modifying enzyme by applying an evaluation method using the proximity effect to the product obtained in the step (i).

(2) A method of assaying the activity of a lipid-modifying enzyme, which comprises the steps of:
 (I) preparing a lipid micelle containing a biotinylated lipid and a substrate for the lipid-modifying enzyme;
 (II) bringing the lipid micelle prepared in the step (I) into contact with the lipid-modifying enzyme; and,
 (III) evaluating the activity of the lipid-modifying enzyme by applying an evaluation method using the proximity effect to the product obtained in the step (II).

(3) The method according to (1) or (2), wherein the lipid-modifying enzyme is selected from the group consisting of a phosphoinositide kinase, a phosphoinositide phosphatase, a phospholipase, a lipase, a sphingomyelinase and a lipid transfer enzyme.

(4) The method according to any one of (1) to (3), wherein the biotinylated lipid is biotinylated phosphatidylethanolamine.

(5) The method according to any one of (1) to (4), wherein the substrate for the lipid-modifying enzyme is selected from the group consisting of phosphatidylinositol (PI), phosphatidylinositol monophosphate (PIP), phosphatidylinositol diphosphate (PIP2), phosphatidylinositol triphosphate (PIP3), phosphatidylcholine, phosphatidylethanolamine and phosphatidylserine.

(6) The method according to any one of (1) to (5), wherein the assay method of the lipid-modifying enzyme activity using said proximity effect is the SPA assay, FRET assay, TR-FRET assay or AlphaScreen assay.

(7) The method according to any one of (1) to (6), wherein the SPA assay is a method using streptavidin-bound SPA beads.

(8) A method of screening a substance inhibiting or promoting the activity of a lipid-modifying enzyme, which comprises the steps of:
 (a) bringing a lipid micelle containing a biotinylated lipid and a substrate for the lipid-modifying enzyme into contact with the lipid-modifying enzyme in the presence or absence of an analyte;
 (b) evaluating the activity of the lipid-modifying enzyme by applying an evaluation method using the proximity effect to the product obtained in the step (a); and,
 (c) comparing the activity of the lipid-modifying enzyme in the presence of the analyte with the activity of the lipid-modifying enzyme in the absence of the analyte to determine that the analyte is a substance inhibiting the activity of the lipid-modifying enzyme or a substance promoting the activity of the lipid-modifying enzyme.

(9) The method according to (8), wherein the activity of inhibiting or promoting the enzyme activity of the analyte is assayed in the presence of a lipid membrane-bound protein having a controlling function to the activity of the lipid-modifying enzyme to be analyzed.

(10) The method according to (9), wherein the lipid membrane-bound protein is a G protein βγ subunit.

(11) The method according to any one of (8) to (11), wherein the lipid-modifying enzyme is selected from the group consisting of a phosphoinositide kinase, a phosphoinositide phosphatase, a phospholipase, a lipase, a sphingomyelinase and a lipid transfer enzyme.

(12) The method according to any one of (8) to (11), wherein the biotinylated lipid is biotinylated phosphatidylethanolamine.

(13) The method according to any one of (8) to (12), wherein the substrate for the lipid-modifying enzyme is selected from the group consisting of phosphatidylinositol (PI), phosphatidylinositol monophosphate (PIP), phosphatidylinositol diphosphate (PIP2), phosphatidylinositol triphosphate (PIP3), phosphatidylcholine, phosphatidylethanolamine and phosphatidylserine.

(14) The method according to any one of (8) to (13), wherein the lipid-modifying enzyme activity assay method using said proximity effect is the SPA assay, FRET assay, TR-FRET assay or AlphaScreen assay.

(15) The method according to any one of (8) to (14), wherein the SPA assay is a method using streptavidin-bound SPA beads.

(16) A method of screening a substance inhibiting or promoting the activity of a lipid-modifying enzyme, which comprises the steps of:
 (d) bringing a lipid micelle containing a biotinylated lipid and a substrate for the lipid-modifying enzyme into contact with the lipid-modifying enzyme in the presence of an analyte, in the presence or absence of a lipid membrane-bound protein having a controlling function to the activity of the lipid-modifying enzyme to be analyzed;
 (e) evaluating the activity of the lipid-modifying enzyme by applying an evaluation method using the proximity effect to the product obtained in the step (d); and,
 (f) comparing the activity of the lipid-modifying enzyme in the presence of the lipid membrane-bound protein with the activity of the lipid-modifying enzyme in the absence of the lipid membrane-bound protein to determine that the analyte is a substance inhibiting the activity of the lipid-modifying enzyme or a substance promoting the activity of the lipid-modifying enzyme through affecting the interactions between the lipid membrane-bound protein and the lipid-modifying enzyme.

According to the present invention, there is provided a novel assay method which can simply determine the activity of the lipid-modifying enzyme. Also, according to the present invention, there is provided a method of efficiently screening a substance which inhibits or promotes the activity of the lipid-modifying enzyme, using this assay method. Furthermore, according to the present invention, there is provided the lipid micelle containing a biotinylated lipid and a substrate for the lipid-modifying enzyme which can be used in these methods.

According to the assay method, the activity of the lipid-modifying enzyme can be assayed in the co-presence of a protein controlling the activity of the lipid-modifying enzyme (controlling protein). Accordingly, not only a substance which directly inhibits or promotes the activity of the lipid-modifying enzyme but also a compound which affects the interactions between the enzyme and the controlling protein can also be screened.

Figure 1:
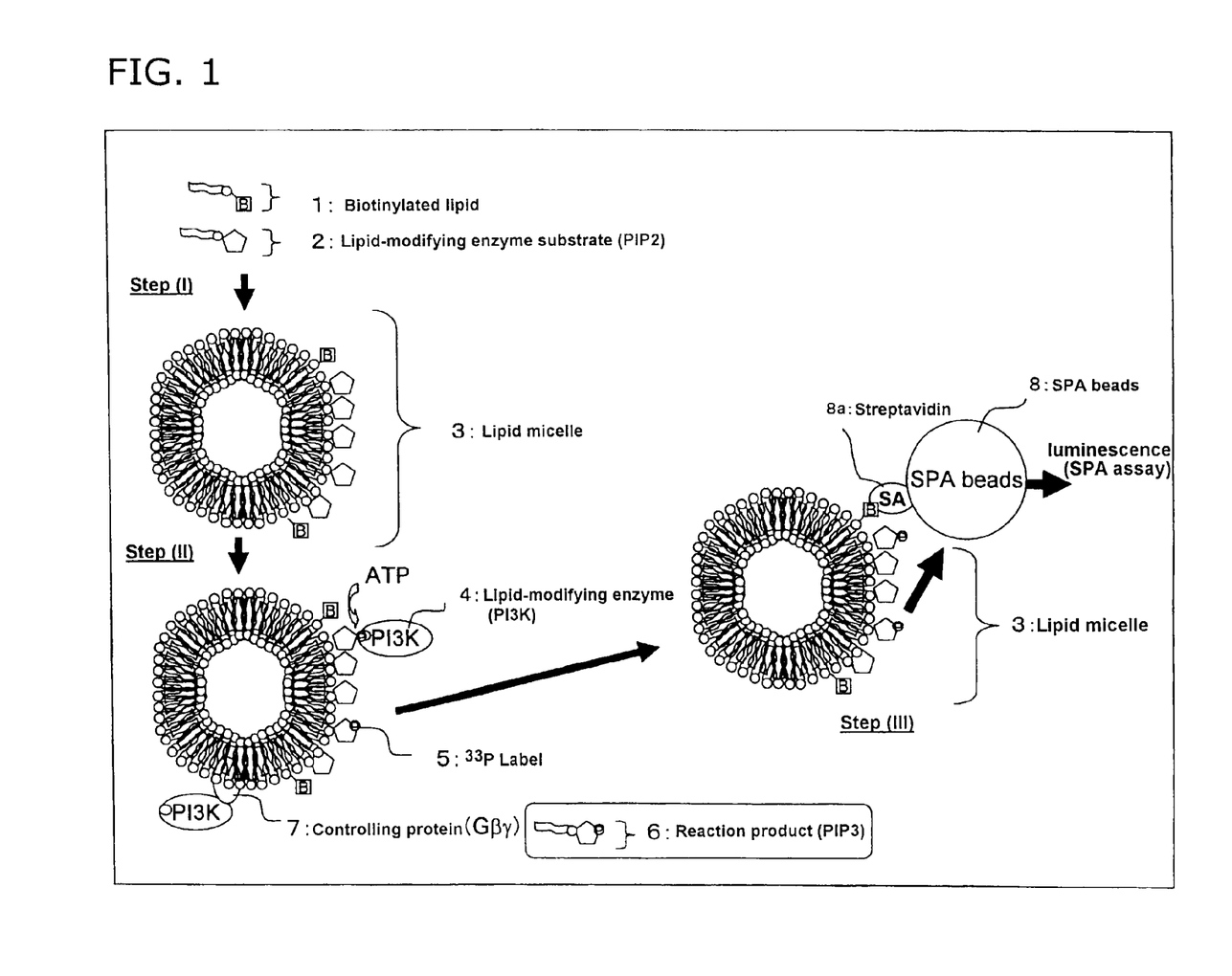
FIG. 1 is a schematic view of the assay method of the present invention.

The symbols used are given below.
1: Biotinylated lipid
2: Substrate for the lipid-modifying enzyme (PIP2)
3: Lipid micelle
4: Lipid-modifying enzyme (PI3K)
5: $^{33}$P label
6: Reaction product (PIP3)
7: Controlling protein (Gβγ)
8: SPA beads
8a: Streptavidin

BEST MODES FOR CARRYING OUT THE INVENTION

Hereinafter, the method of the present invention for assaying the lipid-modifying enzyme, the method of screening a substance which inhibits or promotes the activity of the lipid-modifying enzyme, and so on, are described in detail.

A first embodiment of the present invention relates to a method of assaying the activity of the lipid-modifying enzyme which comprises the steps (i) and (ii) or the steps (I) to (III) below.

(i) the step of bringing a lipid micelle containing a biotinylated lipid and a substrate for the lipid-modifying enzyme into contact with the lipid-modifying enzyme; and, (ii) the step of evaluating the activity of the lipid-modifying enzyme by applying an evaluation method using the proximity effect to the product obtained in the step (i); or, (I) the step of preparing a lipid micelle containing a biotinylated lipid and a substrate for the lipid-modifying enzyme;

(II) the step of bringing the lipid micelle prepared in the step (I) into contact with the lipid-modifying enzyme; and, (III) the step of evaluating the activity of the lipid-modifying enzyme by applying an evaluation method using the proximity effect to the product obtained in the step (II).

As used herein, the term "biotinylated lipid" refers to any compound having a biotin moiety covalently bonded to a lipid molecule. Examples of the biotinylated lipid include N-biotinyl phosphatidylethanolamine, N-biotinyl phosphatidylserine, N-biotinyl phosphatidylcholine, N-biotinyl sphingomyelin, N-biotinyl diacylglycerol, N-biotinyl triacylglycerol, a biotinylated fatty acid, a biotinylated alkyl, etc. Besides the above compounds, the biotinylated lipid may also be a compound as far as it is basically a compound having a lipophilic moiety such as an alkyl of more than $C_4$, etc. and binds to lipid micelles or forms lipid micelles together with other lipid compound.

As used herein, the term "substrate for the lipid-modifying enzyme" means a compound whose structural changes are substantially induced by the lipid-modifying enzyme. Specific examples of the substrate for the lipid-modifying enzyme include but are not limited to the compounds below.

The substrate for the lipid-modifying enzyme which is used in the present invention is a compound with the hydroxyl groups of inositol to be phosphorylated and examples of the substrate include phosphatidylinositol (PI), phosphatidylinositol monophosphate (PIP), phosphatidylinositol diphosphate (PIP2), phosphatidylinositol triphosphate (PIP3), etc for phosphoinositide kinase. Other compounds may also be used as long as they undergo substantial structural changes by phosphoinositide kinase.

The lipid-modifying enzyme substrate for phosphoinositide phosphatase includes a compound that phosphate moieties on the inositol residue are dephosphorylated and examples are phosphatidylinositol monophosphate (PIP), phosphatidylinositol diphosphate (PIP2), phosphatidylinositol triphosphate (PIP3), etc. Other compounds may also be used as long as they undergo substantial structural changes by phosphoinositide phosphatase. The substrate further includes compounds having radioisotopes in the molecule.

The lipid-modifying enzyme substrate for phospholipase is a compound which produces inositol triphosphate, a fatty acid, etc. by cleavage and examples include phosphatidylinositol (PI), phosphatidylinositol monophosphate (PIP), phosphatidylinositol diphosphate (PIP2), phosphatidylcholine, phosphatidylethanolamine, phosphatidylserine, etc. Other compounds may also be used as long as they undergo substantial structural changes by phospholipase. The substrate further includes compounds having radioisotopes in the molecule.

As used herein, the term "lipid-modifying enzyme" means an enzyme that imposes structural changes on a lipid compound by the enzyme action. Specific examples of the lipid-modifying enzyme include phosphoinositide kinase, phosphoinositide phosphatase, phospholipase, lipase, sphingomyelinase, lipid transfer enzyme, etc. Other enzymes may also be used so long as they substantially possess the enzyme action described above. More specific examples of the phosphoinositide kinase include but are not limited to phosphoinositide 3-kinase, phosphoinositide 4-kinase, phosphoinositide 5-kinase, etc. Still more specific examples of the phosphoinositide 3-kinase include but are not limited to phosphoinositide 3-kinase α, phosphoinositide 3-kinase β, phosphoinositide 3-kinase γ, phosphoinositide 3-kinase δ, etc.

Next, the steps (I) to (III) of the present invention will be described below, respectively.

(Step (I): Preparation of Lipid Micelles)

First, the lipid micelle containing the biotinylated lipid and the substrate for the lipid-modifying enzyme is prepared at the step (I) of the present invention.

As used herein, the term "lipid micelle" refers to a micelle made up mainly of an assembly of lipids and generally an assembly formed by orienting the hydrophilic portions of lipids toward the aqueous phase and the hydrophobic portions toward the interior. The lipid micelle also includes those micelles having lipids forming monolayer and bilayer membranes. The shape of the lipid micelle is not particularly limited and includes, for example, spherical and planar shape, but preferably the lipid bilayer membrane forms closed vesicles.

The lipid micelle can be prepared through subjecting a buffer, etc. containing more than a certain concentration of lipids to a physical treatment such as ultrasonication, homogenization, agitation, shaking, freezing and thawing, spraying, etc. The lipid micelle may also be prepared through surfactant treatment, etc.

Lipids which form the lipid micelle are amphoteric lipids having hydrophilic and hydrophobic groups in the lipid molecules. Specific examples include but are not limited to phospholipids, simple lipids (triacylglycerols, diacylglycerols, etc.), glycolipids, glyceroglycolipids, sphingolipids, etc. In addition to these lipids, the lipid micelle may sometimes include fatty acids, fatty acid esters, sphingosine, sterols such as cholesterol, etc. or their esters, and the like.

In order to prepare the lipid micelle containing the biotinylated lipid and the lipid-modifying enzyme substrate in the present invention, the kind of lipid is appropriately chosen. In a specific embodiment of the present invention, the lipid micelle is prepared through modifications of known methods for preparing lipid micelles (e.g., Ref: U. Maier et al., J. Biol. Chem., 274, 29311 (1999)), for example, using biotinyl phosphatidylethanolamine as the biotinylated lipid and phosphatidylinositol diphosphate (PIP2) as the substrate for the lipid-modifying enzyme. In biotinylation of lipids, for example, phosphatidylethanolamine can be biotinylated by reacting with a biotinylation reagent reactive with the amino group or a biotinylation reagent containing a linker and linking the biotin moiety to the ethanolamine residue. Also, phosphatidylethanolserine, phosphatidylethanolcholine, etc. can be biotinylated, for example, by replacing the fatty acid moiety with a fatty acid having a biotin residue. Various biotinylated lipids are described in, e.g., Catalog (2007 January) by Avanti Polar Lipids, Inc. and commercially available. A representative is biotinyl phosphatidylethanolamine which is listed in Catalog Nos. 870282, 870273, 870285, 870277, etc., and other representative biotinylated lipids are listed in Catalog Nos. 860560, 860566, etc., but these compounds are by way of examples and not limited thereto.

Herein, a schematic view of the assay method is shown in FIG. 1, taking as an example the activity assay for phosphoinositide kinase using SPA. As illustrated in Step (I) of FIG. 1, when the biotinylated lipid 1 and the lipid-modifying enzyme substrate 2 (e.g., PIP2) are mixed under conditions to form a lipid micelle, the lipid micelle 3 is prepared. Each one of the biotinylated lipid 1 and the lipid-modifying enzyme substrate 2 are shown in FIG. 1 for brevity but actually a plurality of biotinylated lipids 1 are mixed with a plurality of the lipid-modifying enzyme substrates 2. Symbol [B] denotes biotinyl group in biotinylated lipid 1 and the pentagonal portion denotes phosphorylated sites in the lipid-modifying enzyme substrate 2. Lipid micelle 3 thus prepared has, on its surface, the biotinyl group from biotinylated lipid 1 and the phosphorylation site from the lipid-modifying enzyme substrate 2.

(Step (II): Contact of the Lipid Micelle with the Lipid-Modifying Enzyme)

Next, in Step (II), the lipid micelle prepared in Step (I) is brought into contact with the lipid-modifying enzyme to react the lipid-modifying enzyme substrate in the lipid micelle with the lipid-modifying enzyme.

As illustrated in Step (II) of FIG. 1, the lipid-modifying enzyme (PI3K) 4 is reacted with the lipid micelle 3 containing the lipid-modifying enzyme substrate 2 (PIP2) in the presence of ATP with $^{33}$P-label 5; when PI3K is in an activated state, PIP2 is phosphorylated and converted into PIP3 with $^{33}$P-label (5). This contact step (reaction step) is performed generally in the presence of $Mg^{2+}$ ions at 0 to 50° C., preferably 10 to 40° C. in a buffer of pH 4 to 11, preferably 6 to 8, for 1 second to 1 day, preferably 1 to 300 minutes (cf., Ref: U. Maier et al., J. Biol. Chem., 274, 29311 (1999), etc.).

(Step (III): Evaluation of the Activity of the Lipid-Modifying Enzyme)

Next, in Step (III) of the present invention, the product obtained in Step (II) is evaluated for the activity of the lipid-modifying enzyme using the proximity effect-based evaluation method.

In the present invention, the evaluation method for the activity of the lipid-modifying enzyme using the proximity effect is a method for evaluating the activity of the lipid-modifying enzyme using the proximity effect, including SPA (scintillation proximity assay) method, FRET (fluorescence resonance energy transfer) method, TR-FRET (time-resolved fluorescence resonance energy transfer) method, AlphaScreen method, etc. As used herein, the term "proximity effect" refers to an effect that a signal (e.g., luminescence, fluorescence, etc.) is obtained if X and Y are in close proximity in distance, for the substance (X) binding to the biotin residue contained in the lipid micelle and the radioisotope (Y1) taken up into the substrate for the lipid-modifying enzyme by the lipid-modifying enzyme (or released from the substrate), or for the substance (Y2) having an affinity to the substrate for the lipid-modifying enzyme converted by the lipid-modifying enzyme, or for the substance (Y3) having an affinity to the substrate for the lipid-modifying enzyme before converted by the lipid-modifying enzyme. Therefore, as long as it is a method using the proximity effect, any method can be used in the present invention.

As specific examples of Y2 and Y3 described above, proteins containing the pleckstrin homology (PH) domains in the molecule (PKB/AKT, BTK, GRP1, CH1, DAPP1, PLCδ1, Tih1, Ip1) or partial proteins containing these PH domains can be used to detect phosphatidylinositol which is the substrate or product of phosphoinositide kinase or phosphoinositide phosphatase as the lipid-modifying enzyme, or its phosphorylated forms (A. Saxena et al., J. Biol. Chem., 277, 49935-49944 (2002)). More specifically, partial proteins containing the PH domains of GRP1 can be used to detect phosphoinositol triphosphate (PIP3).

The SPA assay means the scintillation proximity assay technology (Ref: P. B. Fernandes et al., Curr. Opin. Chem. Biol., 1998, 597 (1998)) and is based on the principle that β rays or electron rays emitted from a radioisotope collide with nearby SPA beads and light generated by the collision is measured. SPA beads coated with biotin-binding proteins such as streptavidin, etc., imaging beads, FlashPlate, etc. can be used as X described above. In a preferred embodiment of the present invention, X described above is streptavidin-coated SPA beads and one of Y1 to Y3 is a radioisotope-labeled substance. For example, binding of radioisotope-labeled molecules onto the lipid micelle by enzyme reaction of the lipid-modifying enzyme, or release of radioisotope-labeled molecules from a substrate to which the radioisotope-labeled molecules are bound can be used for Y1 described above. In the case of Y2 and Y3 described above, radioisotope-labeled proteins or antibodies, which specifically bind to a substrate molecule changed after enzyme reaction or to a substrate molecule before changes are induced by enzyme reaction, can be used.

Referring to FIG. 1, the SPA assay is explained below. As illustrated in Step (III), when streptavidin 8a-coated SPA beads 8 are brought in contact with the lipid micelle 3, biotin in the biotinylated lipid 1 binds to streptavidin 8a by the affinity, resulting in binding of SPA beads 8 to the lipid micelle 3. When SPA beads are in close enough proximity to $^{33}$P-labeled PIP3, which is the product from PIP2, SPA beads emit light. By detecting this light emission, the conversion of PIP2 into PIP3, namely, the activation of PI3K can be detected.

The method of the present invention for evaluating the activity using the SPA method is described below in more detail, by way of an example.

Using streptavidin-immobilized SPA beads and a mixture of the lipid micelle containing biotinylated phosphatidylethanolamine and PIP2 as a substrate, enzyme reaction by phosphoinositide 3-kinase is performed in the presence of $^{33}$P-labeled ATP. After the reaction, the beads are washed and counted in a scintillation counter to assay the enzyme activity. According to the method above, upregulation of the enzyme activity can be detected with G-protein βγ subunits known to upregulate the activity of phosphoinositide 3-kinase in the presence of lipid micelles.

Alternatively, enzyme reaction by phosphoinositide 3-kinase is performed in the presence of non-radioactive ATP, using streptavidin-immobilized SPA beads and a mixture of the lipid micelle containing biotinylated phosphatidylethanolamine and PIP2 as substrate. After the reaction, $^{125}$I-labeled GRP-PH domain, which is known to specifically bind to PIP3 produced from PIP2 by the enzyme reaction (Ref: J. K. Klarlund et al., Science, 275, 1927 (1997), Ref: M. P. Czech et al., U.S. Pat. No. 6,221,841, Ref: B. E. Drees et al., U.S. Pat. No. 7,067,269, B. E. Drees et al., US Patent 2005/0009124), is reacted and then counted in a scintillation counter. The enzyme activity can thus be assayed.

The FRET assay method refers to a method using fluorescence resonance energy transfer from a fluorescent donor to a fluorescent acceptor that is generated when two fluorescent substances, fluorescent proteins, etc. are spatially in proximity, and for, e.g., Y2 and Y3 described above, fluorescence-labeled proteins or antibodies, which specifically bind to a substrate molecule changed after enzyme reaction or to a substrate molecule before changes are induced by enzyme reaction, can be used. Fluorescent substances, such as fluorescent proteins, or the like, which are connected with biotin-binding moieties such as proteins, etc., such as streptavidin, etc., can be used as X. Examples of the combination of fluorescent donor and fluorescent acceptor include but are not limited to the combinations of fluorescein and tetramethylrhodamine, tetramethylrhodamine and Texas Red, Eu chelate and Cy5, allophycocyanine or AlexaFluor 647, Tb chelate and fluorescein, rhodamine, BODIPY-TMR or BODIPY-FL, etc.

The TR-FRET assay method refers to a specific method in the FRET assay method above, which uses time-resolved fluorescence and an example is a method of those described above using a lanthanoid ion chelate such as Eu, Tb, Sm, etc. The combination of a fluorescent donor and a fluorescent acceptor includes but are not limited to Eu chelate and Cy5, allophycocyanine or AlexaFluor 647, Tb chelate and fluorescein, rhodamine, BODIPY-TMR or BODIPY-FL, etc.

The method of the present invention for evaluating the activity using the TR-FRET assay method is described below but not limited thereto.

Using the lipid micelle containing biotinyl phosphatidylethanolamine and PIP2 as a substrate, enzyme reaction by phosphoinositide 3-kinase is performed in the presence of non-radioactive ATP. After the reaction, Eu chelate-labeled GRP-PH and biotin-binding streptavidin-labeled allophycocyanine are further added, followed by exposure to light at 340 nm. The enzyme activity can be assayed by measuring the ratio of fluorescence intensity at 665 nm/615 nm.

The AlphaScreen method refers to an assay method, in which singlet oxygen released from donor beads upon exposure to light reaches acceptor beads to generate luminescence due to the proximity effect between the two types of beads (donor and acceptor beads) (Ref: A. Von Leoprechting et al., J. Biomol. Screen., 9, 719 (2004)). In the case of, e.g., Y2 and Y3 described above, proteins or antibodies labeled with a label other than biotin, which specifically bind to a substrate molecule changed after enzyme reaction or to a substrate molecule before changes are induced by enzyme reaction, can be used. Using the label, either the donor or acceptor beads are bound to the proteins or antibodies. Alternatively, the beads can be bound using the antibodies or the beads bound directly can also be used. The other bead to which biotin-binding proteins such as streptavidin, etc. is bound can be used as X. One of the two types of beads described above may be a donor bead and the other may be an acceptor bead.

The method of the present invention for evaluating the activity by the AlphaScreen assay is described below but is not limited to this embodiment.

Using the lipid micelle containing biotinyl phosphatidylethanolamine and PIP2 as a substrate, enzyme reaction by phosphoinositide 3-kinase is performed in the presence of non-radioactive ATP. After the reaction, GRP-PH (tagged with glutathione S-transferase: GST), anti-GST antibody-bound acceptor beads and streptavidin-coated donor beads are added, followed by the measurement according to the AlphaScreen assay, whereby the enzyme activity can be assayed.

According to the method described above, upregulation of the enzyme activity by G protein βγ subunits known to upregulate the activity of phosphoinositide 3-kinase in the presence of the lipid micelle can be detected.

A second embodiment of the present invention relates to a method of screening a substance inhibiting or promoting the activity of the lipid-modifying enzyme, which comprises the steps (a) to (c) below:

(a) bringing a lipid micelle containing a biotinylated lipid and a substrate for the lipid-modifying enzyme into contact with the lipid-modifying enzyme in the presence or absence of an analyte;

(b) evaluating the activity of the lipid-modifying enzyme by applying an evaluation method using the proximity effect to the product obtained in the step (a); and, (c) comparing the activity of the lipid-modifying enzyme in the presence of an analyte with the activity of the lipid-modifying enzyme in the absence of the analyte to determine that the analyte is a substance inhibiting the activity of the lipid-modifying enzyme or a substance promoting the activity of the lipid-modifying enzyme.

The screening method of the present invention provides a method of screening a substance inhibiting or promoting the activity of the lipid-modifying enzyme, using the assay method in accordance with the first embodiment of the present invention described above. Specifically, the reaction of the lipid micelle to the lipid-modifying enzyme in above-described Step (II) is performed in the presence or absence of an analyte in Step (a). Subsequently, the activity of the lipid-modifying enzyme is evaluated as in Step (III) by applying the evaluation method using the proximity effect. Based on the results of evaluation, the activity of the lipid-modifying enzyme in the presence of the analyte is compared with the activity of the lipid-modifying enzyme in the absence of the analyte to determine that the analyte is a compound inhibiting the activity of the lipid-modifying enzyme or a compound promoting the activity of the lipid-modifying enzyme.

Examples of the analyte include a peptide, protein, antibody, non-peptide compound, synthetic compound, fermentation product, cell extract, plant extract, animal cell extract, etc.

As illustrated in Step (II) of FIG. 1, the lipid membrane-bound protein having a controlling function to the activity of the lipid-modifying enzyme to be analyzed (hereinafter also referred to as "controlling protein") can be bound to the lipid micelle in the screening method, which enables to assay the inhibiting or promoting activity of the analyte to the enzymes in the presence of such a lipid membrane-bound protein.

The controlling protein used in the present invention is a controlling protein in response to the intended lipid-modifying enzyme and specific examples include Tyr-phosphorylated receptor, Tyr-phosphorylated proteins, G protein βγ subunit, etc. listed in TABLE 1. These proteins are given by way of example but not limited thereto. In addition to these controlling proteins, there may be additional proteins which control the interactions between the controlling protein and the lipid-modifying enzyme, for example, a protein called an adapter protein or its partial peptide (Ref: T. Pawson and J. D. Scott, Science, 278, 2075 (1997)).

The controlling protein may be a full-length protein or a partial peptide containing a part of its sequence. Examples of the partial peptide include Cys-Gly-Gly-Tyr(P)-Met-Asp-Met-Ser-Lys-Asp-Glu-Ser-Val-Asp-Tyr(P)-Val-Pro-Met-Leu-Asp-Met (SEQ ID NO: 9: cf., Non-Patent Literature 6) having a part of the intracellular sequence region of PDGF (platelet-derived growth factor) receptor, Asn-Gly-Asp-Tyr (P)-Met-Pro-Met-Ser-Pro-Lys-Ser (SEQ ID NO: 10: cf., Ref: H. Kurosu et al., J. Biol. Chem., 272, 24252 (1997)) which is a partial sequence of IRS-1 (insulin receptor substrate-1), and the like. A combination of two or more of the controlling proteins or their partial peptides can also be used.

In the present invention, proteins having naturally occurring amino acid sequences can be used as the controlling proteins and those with modified amino acids can also be used as long as they retain their substantial activity. Proteins with amino acids deleted, substituted or added can be used as well in the present invention. Furthermore, proteins having the reported amino acid sequences which are acquired by means of genetic engineering can be used as they are. Even if the amino acid sequences are appropriately altered by genetic engineering, the resulting proteins can also be used so long as their activities are substantially retained. Furthermore, proteins which have amino acid sequences to facilitate the detection or purification at the amino terminus or the carboxy terminus or in the middle of the sequence of the protein may also be used. Specifically, these amino acid sequences include histidine residue or its consecutive sequence (Poly-His), c-Myc partial peptide (Myc-tag), hemagglutinin partial peptide (HA-tag), Flag partial peptide (Flag-tag), glutathione-S-transferase (GST), maltose-binding protein (MBP), etc. In producing the controlling protein (e.g., trimeric GTP-binding protein β subunit, etc.) by means of genetic engineering, the protein can be produced by introducing the corresponding gene into a vector bearing an appropriate promoter using cells such as animal cells, insect cells, bacteria such as *Escherichia coli*, etc., transfecting the cells with the vector and incubating the cells. A cell-free protein expression system using the extract from *Escherichia coli*, wheat germ extract, etc. may also be used. A synthetic peptide may be used as well.

A more specific example of the controlling protein is a protein (Gβ1γ2-His) obtained by co-expression of G protein β1 subunit (SEQ ID NO: 4) and G protein γ2 subunit (SEQ ID NO: 8), etc.

By comparing the activity of the lipid-modifying enzyme in the presence of the lipid membrane-bound protein to the activity of the lipid-modifying enzyme in the absence of the lipid membrane-bound protein in the screening method described above, it can be determined whether or not the analyte affects the interactions between the lipid membrane-bound protein and the lipid-modifying enzyme and as a result, it can be determined if the analyte is a compound which inhibits the activity of the lipid-modifying enzyme or a compound which promotes the activity of the lipid-modifying enzyme.

A third embodiment of the present invention relates to the lipid micelle containing the biotinylated lipid and the substrate for the lipid-modifying enzyme, which can be used in the method for assaying the activity of the lipid-modifying enzyme and the screening method described above. Herein, biotinyl phosphatidylethanolamine and biotinyl phosphatidylserine are preferred as the biotinylated lipid and phosphatidylinositol diphosphate (PIP2) is preferred as the substrate for the lipid-modifying enzyme.

EXAMPLES

Hereinafter the present invention will be described more specifically by way of example with reference to EXAMPLES, etc. but the scope of the invention is not deemed to be limited thereto.

Example 1

Assay for the Activity of Phosphoinositide 3-Kinase (PI3-Kinase) β Using as a Substrate the Lipid Micelle Containing the Biotinylated Lipid and the PI3-Kinase Substrate as well as the Measurement of Influences by the Addition of G Protein βγ (Gβγ), Using Streptavidin SPA Beads and $^{33}$P-ATP For assaying the activity of phosphoinositide 3-kinase, there is reported a method using the lipid micelle containing phosphatidylinositol [4,5]-diphosphate (PIP2) as a substrate for PI3-kinase and $^{33}$P-ATP as well as imaging beads functioning on the same principle as in SPA beads (Ref: GE Healthcare Life Sciences, Inc., Scientific Poster #132). In this article, it is reported that the activity can be detected with polyethyleneimine-treated beads (PS-PEI) and also with streptavidin beads signals can be detected. Now, the lipid micelle containing PIP2 (PIP2 micelle) in the same manner as above and the lipid micelle containing both PIP2 and the biotinylated lipid to verify the effects by adding the biotinylated lipid in the present invention were prepared, respectively. After mixing with streptavidin SPA beads, it was studied if the $^{33}$P signal was detected by the reaction of PI3-kinase using $^{33}$P-ATP. In this experiment, influences on the PI3-kinase activity were also studied under the respective conditions when G protein βγ was further added.

(1) Preparation of Lipid Micelles

PIP2 micelles: a mixture of phosphatidylethanolamine (0.13 μmol), phosphatidylserine (0.12 μmol), phosphatidylcholine (0.056 μmol), sphingomyelins (0.048 μmol) and phosphatidylinositol [4,5]-diphosphate (0.016 μmol), or PIP2/Biotin-PE micelles: a mixture of PIP2 with 1,2-dipalmitoyl-sn-glycerol-3-phosphoethanolamine-N-(cap biotinyl) (0.10 μmol) (Avanti Polar Lipids, Inc., Product No. 870277P) were placed in a glass tube dried under argon gas. Ice-cold PI3K buffer (0.3 ml) was added to the glass tube, and the mixture was ultrasonicated on ice to prepare two solutions of the lipid micelles (PIP2 micelle and PIP2/Biotin-PE micelle), respectively. The composition of the PI3K buffer is as follows: PI3K buffer (40 mM HEPES-Na (pH7.4), 120 mM NaCl, 1 mM EGTA, 1 mM dithiothreitol, 1 mM β glycerophosphoric acid, 10 mM $MgCl_2$ and 0.1% BSA).

(2) Preparation of G Protein βγ (Gβ1γ2-His)

A Gβ1 expression system using insect cells was constructed as follows. Using synthetic DNAs of SEQ ID NOS: 1 and 2 as primers, PCR was performed in a conventional manner using cDNA clone containing the full-length protein coding region of human Gβ1 as a template. After the resulting DNA of 1051 bp was subcloned into vector pCR4Blunt-TOPO (Invitrogen, Inc., Cat. No. K2875), the nucleotide sequence represented by SEQ ID NO: 3 (SEQ ID NO: 4 shows the amino acid sequence) was confirmed, followed by further cleavage with restriction enzymes EcoRI and XhoI. The resulting fragment was inserted between the same restriction enzyme sites of vector pFastBac1 in the Bac-to-Bac Baculovirus Protein Expression System (Invitrogen, Inc., Cat. No. 10359-016) to prepare pFB1-GNB1. Further according to the manual attached, bacmid DNA was prepared from the culture of transfected *Escherichia coli* DH10Bac strain. This bacmid DNA was transfected into insect cells Sf-21 by the lipofection method to acquire the recombinant virus expressing Gβ1 protein. Following the manual, the virus was further infected to Sf-21 cells to increase the virus titer sufficient to obtain the required level of the recombinant protein. Expression of the target recombinant protein from the virus infected cell extract was confirmed by western blotting using a specific antibody.

A 6×His-Gγ$_2$ ('6×His' disclosed as SEQ ID NO: 11) expression system using insect cells was constructed as follows. Using synthetic DNAs of SEQ ID NOS: 5 and 6 as primers, PCR was performed in a conventional manner with cDNA clone containing the full-length protein coding region of human Gγ$_2$ as a template. After the resulting DNA of 0.3 kbp was subcloned into vector pCR4Blunt-TOPO (Invitrogen, Inc., Catalog No. K2875), the nucleotide sequence represented by SEQ ID NO: 7 (SEQ ID NO: 8 shows the amino acid sequence) was confirmed, followed by cleavage with restriction enzymes EcoRI and XhoI. The resulting fragment was inserted between the same restriction enzyme sites of vector pFastBac1 in the Bac-to-Bac Baculovirus Protein Expression System (Invitrogen, Inc., Catalog No. 10359-016) to prepare pFB1-6×His-GNG2 ('6×His' disclosed as SEQ ID NO: 11). Further according to the manual attached, bacmid DNA was prepared from the culture of transfected *Escherichia coli* DH10Bac strain. This bacmid DNA was transfected to silkworm cells Sf-21 by the lipofection method to acquire the recombinant virus expressing 6×His-Gγ$_2$ protein ('6×His' disclosed as SEQ ID NO: 11). Following the manual, the virus was further infected to Sf-21 cells to increase the virus titer sufficient to obtain the required level of the recombinant protein. Expression of the target recombinant protein from the virus infected cell lysate was confirmed by western blotting using a 6×His tag (SEQ ID NO: 11) sequence-specific antibody.

Production of Gβ1γ2-His using insect cells was performed as follows. The expression and production of Gβ1γ2-His protein using insect cells Sf21 were carried out using the above-described bacmid DNA bearing Gβ1 and Gγ1-His gene, respectively, in accordance with the process described in the instruction manual attached to the Bac-to-Bac Baculovirus Protein Expression System (Invitrogen, Inc., Catalog No. 10359-016). Specifically, baculovirus bearing Gβ1 and Gγ1-His gene, respectively, was charged at MOI of 2 or more in 250 ml volume of Erlenmeyer flask and shake-cultured for 65 hours at 28° C. with $10^8$ cells/100 ml of SF900IISFM medium (Invitrogen, Inc., Catalog No. 10902-096). After culturing, the cells were recovered by centrifugation (1000 rpm, 5 minutes) and washed with insect cell PBS (7.3 mM NaH$_2$PO$_4$ (pH 6.2), 58 mM KCl, 47 mM NaCl and 5 mM CaCl$_2$). By further centrifugation (1000 rpm, 5 minutes), the cells were recovered, frozen and stored.

Gβ1γ2-His was prepared as follows. The cells of 2.5×$10^8$ obtained as described above were suspended in 10 ml of lysis buffer (20 mM HEPES (pH8.0), 150 mM NaCl, 5 mM 2-mercaptoethanol, Protease Inhibitor Cocktail (Roche Diagnostics, Inc., 11-697-498-001), 1 mM EDTA) The suspension was ultrasonicated and then centrifuged at 2600G for 10 minutes to obtain 12 ml of the supernatant. To the supernatant 3 ml of 5% Lubrol was added to make 1% Lubrol. The mixture was stirred at 4° C. for an hour and then centrifuged at 100000G for 20 minutes. The supernatant was obtained as the extract (15 ml). The extract was passed through a column of 500 μl of Ni-NTA agarose (QIAGEN, Inc., Product No. 30210). The column was washed with 1 ml of lysis buffer containing 1% Lubrol and then 2 ml of wash buffer 1 (20mM HEPES (pH 8.0), 0.4M NaCl, 5 mM 2-mercaptoethanol, 0.5% Lubrol, 0.15% sodium cholate, 10 mM imidazole), 2 ml of wash buffer 2 (20 mM HEPES (pH 8.0), 0.1M NaCl, 5 mM 2-mercaptoethanol, 0.25% Lubrol, 0.3% sodium cholate, 10 mM imidazole) and finally 1 ml of wash buffer 3 (20 mM HEPES (pH 8.0), 0.1M NaCl, 5 mM 2-mercaptoethanol, 0.5% sodium cholate, 10 mM imidazole), followed by elution with 1 ml of elution buffer (20 mM HEPES (pH 8.0), 0.01M NaCl, 5 mM 2-mercaptoethanol, 1% sodium cholate, 50 mM imidazole). This eluate was named the Gβ1γ2-His solution. The concentration of Gβ1γ2-His protein was determined by western blotting by comparing with commercially available Gβγ sample (purified protein from bovine brain, Calbiochem, Inc., Product No. 371768) and adjusted to about 100 μg/ml. Hereinafter, this protein is referred to as purified Gβ1γ2-His.

(3) Enzyme Reaction

A 40 mg/ml suspension (200 μl) of streptavidin SPA (scintillation proximity assay) beads (streptavidin SPA beads, GE Healthcare Life Sciences, Inc., Product No. RPNQ0009) was added to each of the two lipid micelle solutions (200 μl) prepared in (1) above. After mixing, each mixture was allowed to stand at an ice temperature for 2 hours (lipid/SPA mixture). To 25 μl of the lipid/SPA mixture, 5 μl of purified Gβ1γ2-His solution (40 μg/ml) (or a solution containing no Gβ1γ2-His), 5 μl of PI3K buffer, 5 μl of PI3-kinase β solution (8 μg/ml) (PI3 Kinase (p110β/p85α) active, Upstate Inc., Product No. 14-603) (or a solution containing no PI3-kinase β) and finally 20 μl ATP solution (10 μl) containing $^{33}$P-γ-ATP were sequentially added to initiate the reaction. Approximately 74 kBq of $^{33}$P-γ-ATP was added per reaction. The reaction was carried out at room temperature for 40 minutes. After SPA beads were washed, the SPA beads were suspended in 100 μl of PI3K buffer and $^{33}$P was counted on a white 96-well plate using TopCount (Packard Instrument Co.).

(4) Measurement Results of Enzyme Reaction

Figure 2:
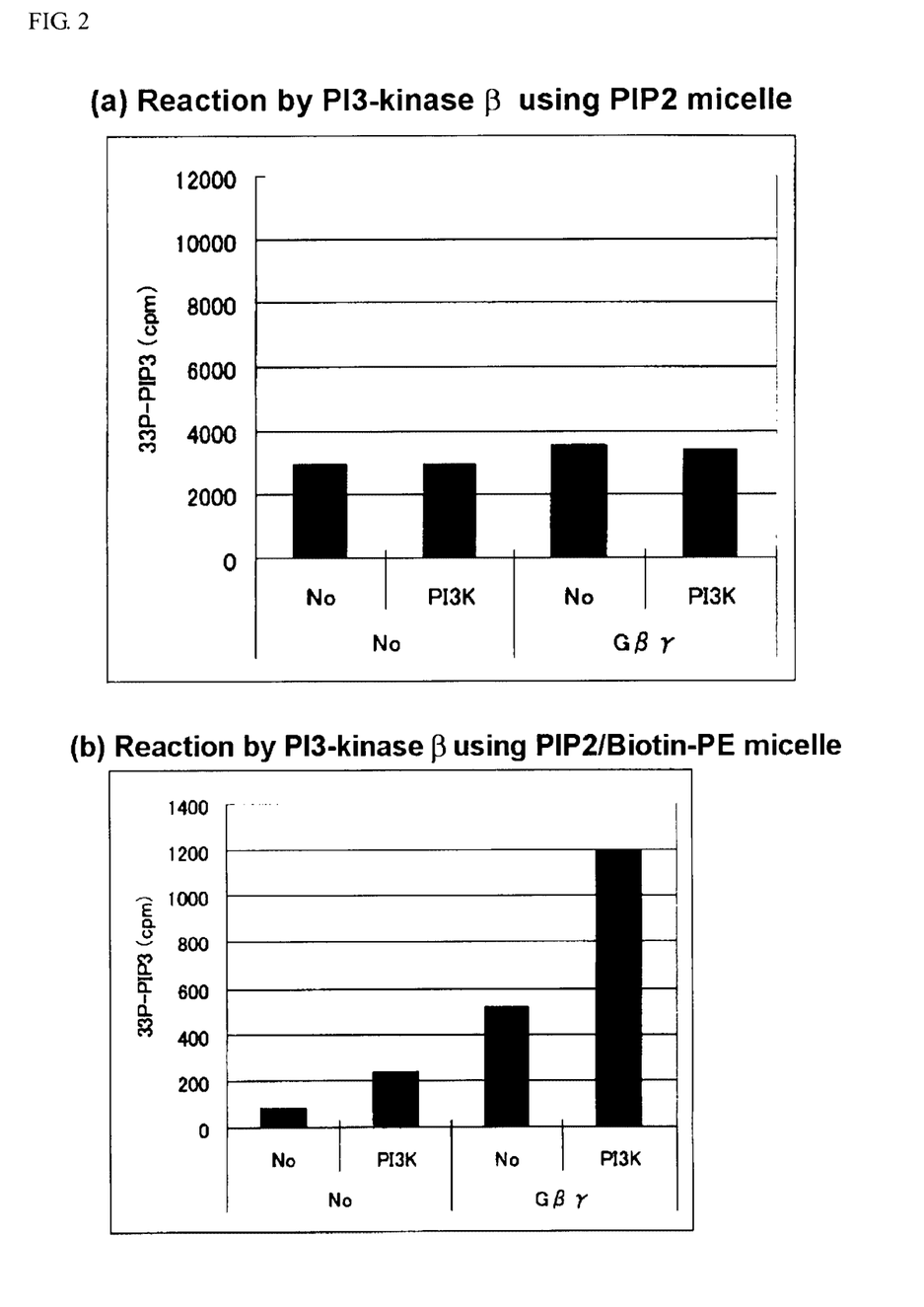
FIG. 2 illustrates the measurement of the activity of phosphoinositide 3-kinase (PI3-kinase) β by using as a substrate the lipid micelle containing the PI3 kinase substrate with or without addition of the biotinylated lipid with streptavidin SPA beads and $^{33}$P-ATP, as well as influences by the addition of G protein βγ (Gβγ), wherein (a) indicates the data obtained through the reaction by PI3-kinase β using the PIP2 micelle (without addition of the biotinylated lipid) and (b) indicates the data obtained through the reaction by PI3-kinase β using the PIP2/Biotin-PE micelle (by addition of the biotinylated lipid).

The results obtained using the PIP2 micelles without addition of the biotinylated lipid are shown in FIG. 2(a) and the results obtained using the PIP2/Biotin-PE micelles with addition of the biotinylated lipid in FIG. 2(b). In the reaction using the PIP2 micelles, no signal due to PI3-kinase β was observed, regardless of the presence or absence of Gβ1γ2-His, whereas in the reaction using the PIP2/Biotin-PE micelles, signals increased by the addition of PI3-kinase β and more increased signals in the presence of Gβ1γ2-His were observed. The results reveal that the activity of PI3-kinase β and upregulation of the activity by Gβγ can be assayed by the method using the lipid micelle containing the biotinylated lipid and PIP2. At the same time, the results also reveal that the detectability was obviously improved as compared to the known method (GE Healthcare Life Sciences, Inc., Scientific Poster #132).

Example 2

Assay for the Activity of Phosphoinositide 3-Kinase (PI3-Kinase) α Using as a Substrate the Lipid Micelle Containing the Biotinylated Lipid and the PI3-Kinase Substrate, Using Streptavidin SPA Beads and $^{125}$I-Labeled GRP-PH (1) $^{125}$I-Labeling of GRP-PH It is known that GRP-PH is a protein, which does not bind to phosphatidylinositol [4,5]-diphosphate (PIP2) and selectively binds to phosphatidylinositol-[3,4,5] triphosphate (PIP3) produced from PIP2 by phosphoinositide 3-kinase (PI3-kinase), and can be used to detect the reaction of PI3-kinase (Ref: J. K. Klarlund et al., Science, 275, 1927 (1997), Ref: M. P. Czech et al., U.S. Pat. No. 6,221,841, Ref: B. E. Drees et al., U.S. Pat. No. 7,067,269, Ref: B. E. Drees et al., US Patent 2005/0009124). In this EXAMPLE, labeling of commercially available GRP-PH (Cell Biolabs, Inc., Product No. STA-200) with $^{125}$I was first performed by the Iodogen method.

In a 5 ml polypropylene tube, 0.5 ml of 1 mg/ml chloroform solution of Iodogen (Pierce Inc., Product No. 28600) was charged and dried in an argon gas. A 0.5 ml of TBS (Tris-buffered saline: 20 mM Tris-HCl (pH7.4), 150 mM NaCl) containing the above GRP-PH (20 μg) was put in the polypropylene tube, and 5 μl (18.5 MBq) of Na$^{125}$I (PerkinElmer, Inc., Product No. NEZ033A) was added thereto. The mixture was reacted at room temperature for 2 minutes. The reaction mixture was passed through a PD10 column (GE Healthcare Life Sciences, Inc., Product No. 17-0851-01), which had been blocked with TBS solution containing 10% BSA (bovine serum albumin) and thoroughly washed with TBS. After washing the column with 3 ml of TBS, 1 ml of the subsequent eluate was fractionated, frozen and stored as the $^{125}$I-labeled GRP-PH solution.

(2) Detection of the Reaction Using PI3-Kinase α

Figure 3:
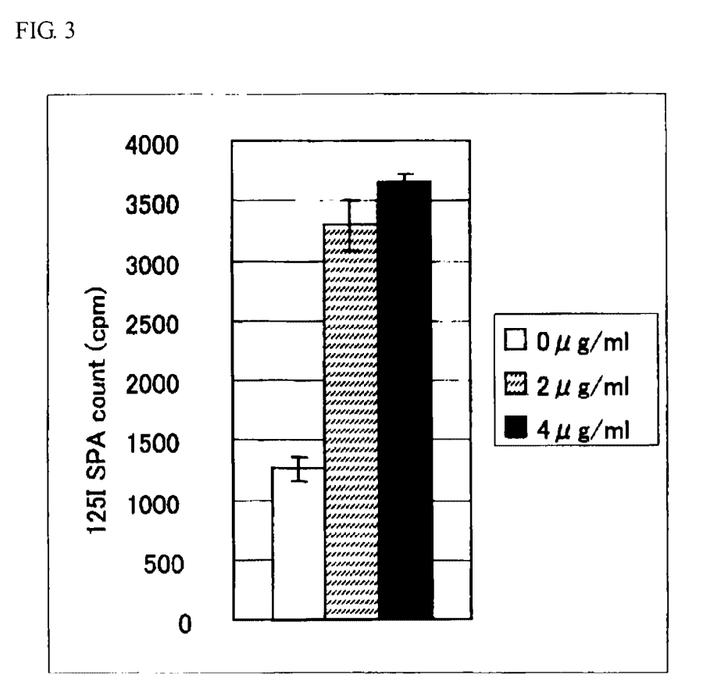
FIG. 3 illustrates the measurement of the activity of phosphoinositide 3-kinase (PI3-kinase) α using as a substrate the lipid micelle containing the biotinylated lipid and the PI3 kinase substrate, using streptavidin SPA beads and $^{125}$I-labeled GRP-PH.

PIP2/Biotin-PE micelles were prepared by the same procedure as described in EXAMPLE 1, except that the amount of PI3K buffer used for the suspension was changed to 400 μl. A 40 mg/ml suspension of streptavidin SPA beads (GE Healthcare Life Sciences, Inc., Product No. RPNQ0009) was added in an equal volume to the micelle solution to prepare the lipid/SPA solution mixture. To 110 μl of the lipid/SPA solution mixture, 2.2 μl of PI3-kinase α (PI3 Kinase (p110β/p85α), active, Upstate, Inc., Product No. 14-602) (0, 100 and 200 μg/ml at final concentrations, respectively, 0, 2 and 4 μg/ml) and 1.1 μl of 40 mM ATP were added in this order. The mixture was reacted at room temperature for an hour. After the reaction, 50 μl of PI3K buffer containing 0.5% BSA and 2.5 μM wortmannin, 25 μl of the reaction solution and further 25 μl of the above $^{125}$I-labeled GRP-PH solution diluted to 0.2 μg/ml were loaded onto a white 96-well plate. After mixing them, the mixture was allowed to stand at room temperature overnight, followed by determination of $^{125}$I using TopCount (Packard Instrument Co.). As shown in FIG. 3, an increase in $^{125}$I counts by the enzyme addition, namely, the PI3K reaction, was detected.

Example 3

Figure 4:
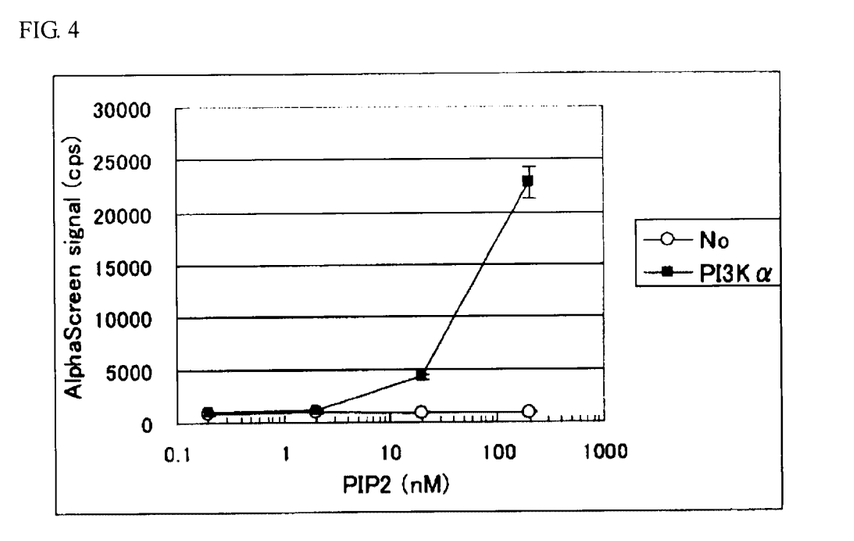
FIG. 4 illustrates the measurement of the activity of phosphoinositide 3-kinase (PI3-kinase) α using as a substrate the lipid micelle containing the biotinylated lipid and the PI3 kinase substrate, by the AlphaScreen assay.

Assay for the Activity of Phosphoinositide 3-Kinase (PI3-Kinase) α Using as a Substrate the Lipid Micelle Containing the Biotinylated Lipid Substrate and the PI3-Kinase Substrate, by the AlphaScreen Assay PIP2/Biotin-PE micelles were prepared by the same procedure as described in EXAMPLE 1, except that the amount of PI3K buffer used for the suspension was changed to 360 μl. To 49 μl of the micelle solution, 49 μl of PI3K buffer (the BSA concentration was changed to 0.01%) was added, and 1 μl of PI3-kinase α (200 μg/ml) (PI3 Kinase (p110β/p85α), active, Upstate, Inc., Product No. 14-602) (or a solution containing no PI3-kinase α) and 1 μl of 40 mM ATP were further added sequentially to the mixture. The mixture was reacted at room temperature and an hour after, PI3K buffer (11 μl) containing 100 μM wortmannin and 1% BSA was added to stop the reaction. After the reaction, 5 μl of 0.1% BSA-containing PI3K buffer solution of GRP-PH (10 nM) (Cell Biolabs, Inc., Product No. STA-200) and 10 μl of the reaction solution serially diluted with 0.1% BSA-containing PI3K buffer were loaded onto a white 384-well plate. The mixture was allowed to stand at room temperature for 30 minutes. Furthermore, 5 μl of a 50-fold dilution of anti-GST acceptor beads in 0.1% BSA-containing PI3K buffer was added to the mixture in accordance with the manual attached to the AlphaScreen GST Detection Kit (PerkinElmer Inc., Product No. 6760603C). The mixture was allowed to stand at room temperature for 30 minutes. Then, 5 μl of streptavidin donor beads likewise diluted to 50-fold was added to the mixture. After the mixture was allowed to stand at room temperature for 2 hours, measurement was performed on EnVision (Perkin Elmer, Inc.) according to the AlphaScreen assay protocol. Relationship between the PIP2 concentration basically contained in each reaction dilution and the signal values measured is shown in FIG. 4. As shown in FIG. 4, signals relative to the PIP3 produced by the reaction were observed in the PI3-kinase α-added samples, indicating that the activity of PI3-kinase can be detected using this method.

Example 4

Assay for the Activity of Phosphoinositide 3-Kinase (PI3-Kinase) α Using as a Substrate the Lipid Micelle Containing the Biotinylated Lipid and the PI3-Kinase Substrate, by the TR-FRET Assay In a manner similar to the procedure of EXAMPLE 3, the reaction was carried out with the addition of PI3-kinase α (final concentration of 2 μg/ml) or without the addition of the enzyme and the reactant dilutions were prepared in the same way.

"Detection Mixture" of PI3-Kinase (human) HTRF Assay Kit (Upstate Biotechnology, Inc., Product No. 33-016), which contains a fluorescent donor binding to biotinylated PIP3 and PIP3 (PIP3-binding protein (GST tagged), Eu chelate-labeled anti-GST antibody) and a fluorescent acceptor (streptavidin-labeled APC) and enables detection of PIP3 by the TR-FRET method was prepared according to the protocol attached to the kit.

Figure 5:
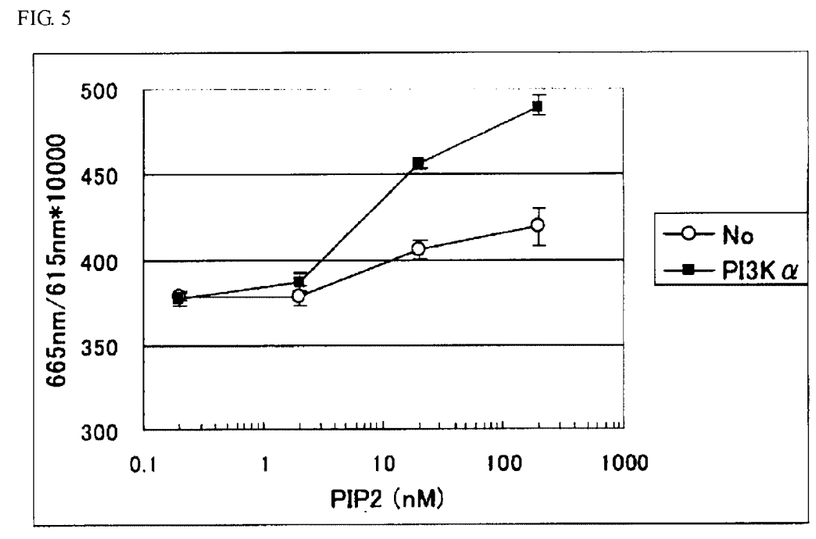
FIG. 5 illustrates the measurement of the activity of phosphoinositide 3-kinase (PI3-kinase) α using as a substrate the lipid micelle containing the biotinylated lipid and the PI3-kinase substrate, by the TR-FRET assay.

To a white 384-well plate, 10 μl of 0.1% BSA-containing PI3K buffer, 10 μl of the reaction dilution described above and 5 μl of "Detection Mixture" prepared above were loaded into a white 384-well plate in this order. After the mixture was allowed to stand at room temperature for about 3 hours, the time-resolved fluorescence was measured at 615 nm and 665 nm on EnVision (PerkinElmer, Inc.) according to the assay protocol suitable for HTRF. Relationship between the PIP2 concentration basically contained in each reaction dilution and the signal values measured is shown in FIG. 5. As shown in FIG. 5, signals relative to PIP3 produced by the reaction were observed in the PI3-kinase α-added samples, indicating that the activity of PI3-kinase can be detected using this method.

Example 5

Assay for the Activity of Phosphoinositide 3-Kinase (PI3-Kinase) β Using as a Substrate the Lipid Micelle Containing the Biotinylated Lipid and the PI3-Kinase Substrate as Well as the Measurement of Influences By the Addition of G Protein βγ (Gβγ), By the AlphaScreen Assay

(1) Preparation of Lipid Micelles

A mixture of phosphatidylethanolamine (0.26 μmol), phosphatidylserine (0.24 μmol), phosphatidylcholine (0.11 μmol), sphingomyelins (0.096 μmol) and phosphatidylinositol [4,5]-diphosphate (0.032 μmol) with 1,2-dipalmitoyl-sn-glycerol-3-phosphoethanolamine-N-(cap biotinyl) (0.20 μmol) (Avanti Polar Lipids, Inc., Product No. 870277P) were placed in a glass tube dried under argon gas, and PI3K buffer (0.8 ml) at an ice temperature was added to the mixture. The resulting mixture was ultrasonicated on ice to prepare the PIP2/Biotin-PE micelle solution. The composition of the PI3K buffer is as follows: PI3K buffer (40 mM HEPES-Na (pH7.4), 120 mM NaCl, 1 mM EGTA, 1 mM dithiothreitol, 1 mM 3 μlycerophosphoric acid, 10 mM $MgCl_2$ and 0.01% BSA).

(2) Measurement of the PI3-Kinase β Activity and Measurement of Influences by the Addition of G Protein βγ (Gβγ)

Figure 6:
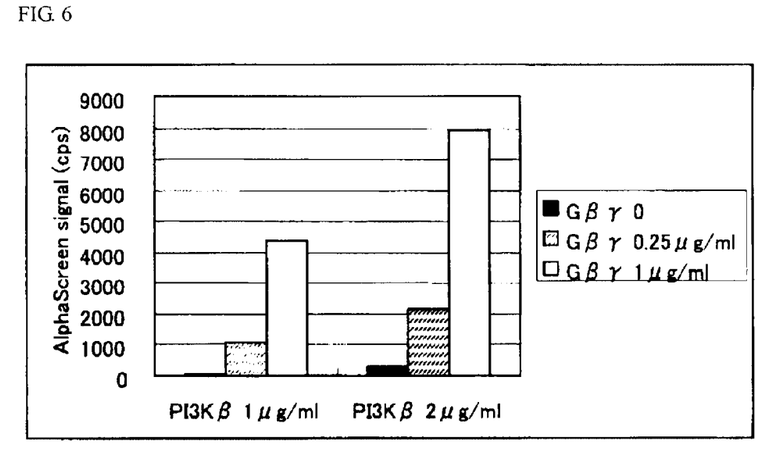
FIG. 6 illustrates the measurement of the activity of phosphoinositide 3-kinase (PI3-kinase) β using as a substrate the lipid micelle containing the biotinylated lipid and the PI3-kinase substrate by the AlphaScreen assay, and the measurement of influences by the addition of G protein βγ (Gβγ).

The above PIP2/Biotin-PE micelle solution was diluted to 100-fold in PI3K buffer, and Gβ1γ2-His (final concentrations of 0, 0.25 and 1 μg/ml) purified by the same procedure as described in EXAMPLE 1 and PI3-kinase β (final concentrations of 0, 1 and 2 μg/ml) (PI3 Kinase (p110β/p85α), active, Upstate Inc., Product No. 14-603) were added to the dilution. To 20 μl of the resulting solution, 5 μl of 2.4 mM ATP was added, and the mixture was then reacted at room temperature for an hour. To stop the reaction, 15 μl of PI3K buffer containing 30 μM wortmannin, 10 nM GRP-PH (Cell Biolabs Inc., Product No. STA-200) and 0.3% BSA was added to the mixture, and the reaction mixture was allowed to stand at room temperature for 30 minutes. To a white 384-well plate, 5 μl of a 50-fold dilution of anti-GST acceptor beads diluted in 0.1% BSA-containing PI3K buffer and 15 μl of the reaction solution above were added in accordance with the manual attached to the AlphaScreen GST Detection Kit (PerkinElmer Inc., Product No. 6760603C). The mixture was allowed to stand at room temperature for 30 minutes. To the mixture, 5 μl of streptavidin donor beads likewise diluted to 50-fold was further added. After the mixture was allowed to stand at room temperature for 1.5 hours, the measurement was performed on EnVision (PerkinElmer, Inc.) according to the AlphaScreen assay protocol. The signal values at the respective concentrations of Gβγ added are shown in FIG. 6. The values after subtraction of the signal values for a sample without addition of both PI3-kinase β and Gβ1γ2-His are expressed as the signal values produced by the enzyme activity. As shown in FIG. 6, the activity of PI3-kinase β was observed as the signal value due to PIP3, which was produced in the reaction, and upregulation of the PI3-kinase β activity dependent on the level of Gβγ added was seen. It was revealed that upregulation of the activity of PI3-kinase β relative to Gβγ can be assayed by using this method, indicating that a compound affecting (promoting or inhibiting) the interactions of PI3-kinase β/Gβγ can be screened using this method.

Screening of the inhibitor or promotor for the activity of the lipid-modifying enzyme can be performed, for example, by evaluating the activity of the lipid-modifying enzyme in the presence or absence of an analyte, by modifications of the procedures described in EXAMPLES 1 to 5 above.

In addition, the substance which affects the interactions between the lipid membrane-bound protein and the lipid-modifying enzyme can be screened, for example, as in EXAMPLE 5, by evaluating an analyte for the function of inhibiting/promoting the activity of the lipid-modifying enzyme in the presence or absence of the lipid membrane-bound protein having a controlling function to the activity of the lipid-modifying enzyme.

Industrial Applicability

By using the screening method of the present invention, the inhibitor or promotor for the lipid-modifying enzyme can be obtained. For example, the inhibitor for phosphoinositide kinase can be used as an anti-inflammatory agent, an anti-cancer agent, etc. and the promotor can be used as a drug for the treatment of diabetes mellitus.

---

The invention claimed is:

1. A method of assaying the activity of a lipid-modifying enzyme, wherein the method comprises:
   bringing a lipid micelle comprising a biotinylated lipid and a substrate for the lipid-modifying enzyme into contact with the lipid-modifying enzyme to obtain a product; and
   evaluating the activity of the lipid-modifying enzyme by applying an evaluation method using a proximity effect to the product obtained from said bringing.

2. The method according to claim 1, wherein the method further comprises:
   preparing a lipid micelle comprising a biotinylated lipid and a substrate for the lipid-modifying enzyme;
   bringing the lipid micelle obtained from said preparing into contact with the lipid-modifying enzyme to obtain a product; and
   evaluating the activity of the lipid-modifying enzyme by applying an evaluation method using a proximity effect to the product obtained from said bringing.

3. The method according to claim 1, wherein the lipid-modifying enzyme is selected from the group consisting of a phosphoinositide kinase, a phosphoinositide phosphatase, a phospholipase, a lipase, a sphingomyelinase and a lipid transfer enzyme.

4. The method according to claim 1, wherein the biotinylated lipid is biotinylated phosphatidylethanolamine.

5. The method according to claim 1, wherein the substrate for the lipid-modifying enzyme is selected from the group consisting of phosphatidylinositol (PI), phosphatidylinositol monophosphate (PIP), phosphatidylinositol diphosphate (PIP2), phosphatidylinositol triphosphate (PIP3), phosphatidylcholine, phosphatidylethanolamine and phosphatidylserine.

6. The method according to claim 1, wherein the method of assaying the activity of the lipid-modifying enzyme using said proximity effect is a scintillation proximity assay (SPA), a FRET assay, a TR-FRET assay or a amplified luminescent proximity homogeneous assay.

7. The method according to claim 6, wherein the SPA assay is a method using streptavidin-bound SPA beads.

8. A method of screening a substance inhibiting or promoting the activity of a lipid-modifying enzyme, wherein the method comprises:
   bringing a lipid micelle comprising a biotinylated lipid and a substrate for the lipid-modifying enzyme into contact with the lipid-modifying enzyme in the presence or absence of an analyte to obtain a product;
   evaluating the activity of the lipid-modifying enzyme by applying an evaluation method using a proximity effect to the product obtained from said bringing; and
   comparing the activity of the lipid-modifying enzyme in the presence of an analyte with the activity of the lipid-modifying enzyme in the absence of the analyte to determine that the analyte is a substance inhibiting the activity of the lipid-modifying enzyme or a substance promoting the activity of the lipid-modifying enzyme.

9. The method according to claim 8, wherein the activity of inhibiting or promoting the enzyme activity of the analyte is assayed in the presence of a lipid membrane-bound protein having a controlling function to the activity of the lipid-modifying enzyme to be analyzed wherein the lipid-modifying enzyme is phosphoinositide 3-kinase and the lipid membrane-bound protein is a G protein $\beta\gamma$ subunit.

10. The method according to claim 8, wherein the lipid-modifying enzyme is selected from the group consisting of a phosphoinositide kinase, a phosphoinositide phosphatase, a phospholipase, a lipase, a sphingomyelinase and a lipid transfer enzyme.

11. The method according to claim 8, wherein the biotinylated lipid is biotinylated phosphatidylethanolamine.

12. The method according to claim 8, wherein the substrate for the lipid-modifying enzyme is selected from the group consisting of phosphatidylinositol (PI), phosphatidylinositol monophosphate (PIP), phosphatidylinositol diphosphate (PIP2), phosphatidylinositol triphosphate (PIP3), phosphatidylcholine, phosphatidylethanolamine and phosphatidylserine.

13. The method according to claim 8, wherein the method of screening a substance inhibiting or promoting the activity of a lipid-modifying enzyme using said proximity effect is a SPA assay, a FRET assay, a TR-FRET assay or a amplified luminescent proximity homogeneous assay.

14. The method according to claim 13, wherein the SPA assay is a method using streptavidin-bound SPA beads.

15. A method of screening a substance inhibiting or promoting the activity of a lipid-modifying enzyme, wherein the method comprises:
   bringing a lipid micelle comprising a biotinylated lipid and a substrate for the lipid-modifying enzyme into contact with the lipid-modifying enzyme in the presence of an analyte, and in the presence or absence of a lipid membrane-bound protein having a controlling function to the activity of the lipid-modifying enzyme to be analyzed to obtain a product;
   evaluating the activity of the lipid-modifying enzyme by applying an evaluation method using a proximity effect to the product obtained from said bringing; and
   comparing the activity of the lipid-modifying enzyme in the presence of the lipid membrane-bound protein with the activity of the lipid-modifying enzyme in the absence of the lipid membrane-bound protein to determine that the analyte is a substance inhibiting the activity of the lipid-modifying enzyme or a substance promoting the activity of the lipid-modifying enzyme through affecting interactions between the lipid membrane-bound protein and the lipid-modifying enzyme wherein the lipid-modifying enzyme is phosphoinositide 3-kinase and the lipid membrane-bound protein is a G protein $\beta\gamma$ subunit.

* * * * *